United States Patent
Wang et al.

(10) Patent No.: US 11,268,946 B2
(45) Date of Patent: Mar. 8, 2022

(54) LIFE-CYCLE PERFORMANCE INTELLIGENT-SENSING AND DEGRADATION WARNING SYSTEM AND METHOD FOR CONCRETE STRUCTURES

(71) Applicant: QINGDAO UNIVERSITY OF TECHNOLOGY, Qingdao (CN)

(72) Inventors: Penggang Wang, Qingdao (CN); Zuquan Jin, Qingdao (CN); Tiejun Zhao, Qingdao (CN); Dongshuai Hou, Qingdao (CN); Li Tian, Qingdao (CN); Peng Zhang, Qingdao (CN); Xiaomei Wan, Qingdao (CN); Siyao Guo, Qingdao (CN); Yupeng Tian, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 0 days.

(21) Appl. No.: 17/286,829

(22) PCT Filed: Jun. 11, 2020

(86) PCT No.: PCT/CN2020/095588
§ 371 (c)(1),
(2) Date: Apr. 20, 2021

(87) PCT Pub. No.: WO2021/031664
PCT Pub. Date: Feb. 25, 2021

(65) Prior Publication Data
US 2021/0356451 A1 Nov. 18, 2021

(30) Foreign Application Priority Data
Aug. 22, 2019 (CN) .......................... 201910778440.2

(51) Int. Cl.
*G01N 33/38* (2006.01)
*G08B 3/10* (2006.01)
(Continued)

(52) U.S. Cl.
CPC ............. *G01N 33/383* (2013.01); *G08B 3/10* (2013.01); *G08B 13/19656* (2013.01); *G08B 21/182* (2013.01); *H04N 7/183* (2013.01)

(58) Field of Classification Search
CPC .. G01N 33/383; G08B 3/10; G08B 13/19656; G08B 21/182; H04N 7/183
See application file for complete search history.

(56) References Cited

U.S. PATENT DOCUMENTS

| 7,038,470 B1* | 5/2006 | Johnson | G01N 27/226 250/390.05 |
| 2002/0057097 A1* | 5/2002 | Kelly | G01N 17/006 324/700 |

(Continued)

FOREIGN PATENT DOCUMENTS

| CN | 105116134 A | 12/2015 |
| CN | 104075756 B | 9/2016 |

(Continued)

*Primary Examiner* — Ryan W Sherwin
(74) *Attorney, Agent, or Firm* — Bayramoglu Law Offices L.L.C (57) ABSTRACT

A life-cycle performance intelligent-sensing and degradation warning system and method for concrete structures are disclosed. The warning system comprises a main control module, a multifunctional sensor module, an anti-theft module and a critical warning module. Environmental parameters in concrete are monitored by the multifunctional sensor module, and the remaining service life of a concrete structure is accurately predicted through a life prediction model according to the temperature, humidity, chloride ion concentration and pH at different depths, and a critical chloride ion concentration and a structure stress status that are (Continued)

dynamically obtained. In addition, during warning analysis, a targeted correction method is designed for acquired data, and temperature and pH correction is carried out for real-time monitoring data of the chloride ion sensor to further guarantee the accuracy of monitoring data, such that scientific references are provided for durability evaluation, protection and restoration of the structure.

9 Claims, 3 Drawing Sheets

(51) Int. Cl.
*G08B 13/196* (2006.01)
*G08B 21/18* (2006.01)
*H04N 7/18* (2006.01)

(56) References Cited

U.S. PATENT DOCUMENTS

| | | | |
|---|---|---|---|
| 2014/0249788 | A1 | 9/2014 | Marchand et al. |
| 2016/0266086 | A1* | 9/2016 | Von Herzen .......... E21B 47/005 |
| 2016/0274001 | A1* | 9/2016 | Parker .................... G01B 11/16 |
| 2018/0238820 | A1* | 8/2018 | Ghods .................... G01N 17/02 |
| 2019/0120707 | A1* | 4/2019 | Chung ................. G01N 33/383 |

FOREIGN PATENT DOCUMENTS

| | | |
|---|---|---|
| CN | 106053326 A | 10/2016 |
| CN | 205898650 U | 1/2017 |
| CN | 108469514 A | 8/2018 |
| CN | 108680490 A | 10/2018 |
| CN | 109374726 A | 2/2019 |
| CN | 110567513 A | 12/2019 |

* cited by examiner

LIFE-CYCLE PERFORMANCE INTELLIGENT-SENSING AND DEGRADATION WARNING SYSTEM AND METHOD FOR CONCRETE STRUCTURES

CROSS REFERENCE TO THE RELATED APPLICATIONS

This application is the national phase entry of International Application No. PCT/CN2020/095588, filed on Jun. 11, 2020, which is based upon and claims priority to Chinese Patent Application No. 201910778440.2, filed on Aug. 22 2019, the entire contents of which are incorporated herein by reference.

TECHNICAL FIELD

The invention belongs to the technical field of performance tests of civil engineering materials, and particularly relates to a life-cycle performance intelligent-sensing and degradation warning system and method for concrete structures.

BACKGROUND

Micro-environmental conditions of the internal structure of reinforced concrete structures determine the corrosion of steel bars, thus affecting the service life of the reinforced concrete structures in service, wherein the micro-environmental conditions of the internal structure typically include the parameters such as temperature, humidity, pH, chloride ion concentration, stress and strain. Particularly, in the marine environment, the reinforced concrete structures are often subject to chloride ion erosion and thus may degrade too early.

The reinforced concrete structures at home and abroad are facing the severe problem of durability. According to the statistics, steel bars of harbor projects constructed before the 1990's in China have been seriously corroded after being used for 10-20 years. The most direct and effective method to dynamically acquire the internal micro-environmental factors of the reinforced concrete structures is to monitor the durability of the reinforced concrete structures, which can accurately sense the service life and predict the degradation of the reinforced concrete structure to provide references for later protection and restoration. Most devices for monitoring the internal micro-environmental factors of concrete on the present market work independently, which is not beneficial for synchronous acquisition of signals.

Former studies have indicated that whether or not steel bars in concrete in the marine environment will be corroded depends on the coupling effect of various factors in the internal micro-environment (such as temperature, humidity, pH, chloride ion concentration, stress and strain), so it is necessary to know the micro-environment of concrete structures in the marine environment in real time and the corrosion condition of steel bars in the concrete structures and to obtain the change rule of these performance parameters over time to provide important references for the safety and restoration of projects. Chinese Invention Patent Authorization and Publication No. CN104075756B discloses a multi-element compound wireless detection system for concrete durability, which can monitor the humidity, temperature and pH in concrete and the corrosion condition of steel bars in concrete. However, this technical solution does not provide a specific parameter correction method and does not point out how to use these parameters either.

As is known to all, the internal temperature of concrete structures will change with the variation of the temperature of the service environment, and chloride ion sensors and pH sensors buried in concrete will also be influenced by the temperature, so the test results of these sensors will be inaccurate without correction. In addition, the interior of hardened concrete is generally strongly alkaline and has a pH greater than 12.5. Carbon dioxide in the atmosphere may react with calcium hydroxide in the concrete to generate neural calcium carbonate, which can reduce the pH of the concrete. Moreover, some acid gases or acid liquids in certain industrial environments may neutralize the concrete, and the chloride ion sensors buried in the concrete will be affected by the pH, so the test results of the chloride ion sensors will be inaccurate without correction, which leads to a misjudgment on the critical state of the reinforced concrete structures.

A large number of researches on the critical chloride ion concentration have been made at home and abroad, which indicate that the critical chloride ion concentration is generally affected by the $C_3A$ content, alkali content and sulfate content of cement, the fly ash content, mineral powder content, silicon ash content and limestone powder content of concrete, the type of steel bars, the construction quality, the service environment and the like and the critical chloride ion concentration of reinforced concrete structures in different environment varies drastically. In the prior art, there are three methods for expressing the critical chloride ion concretion: total chloride ion concentration method, free chloride ion concentration method and $[Cl^-]/[OH^-]$ method. As reported by related documents, the critical chloride ion concentration expressed by the total chloride ion concentration method is the total chloride ion concentration which accounts for 0.17-2.45% of the weight of cementing materials, the critical chloride ion concentration expressed by the free chloride ion concentration method is the free chloride ion concentration which accounts for 0.11-0.48% of the weight of cementing materials, and the critical chloride ion concentration expressed by the $[Cl^-]/[OH^-]$ method is the $[Cl^-]/[OH^-]$ ratio which is 0.12-40%. As can be seen the critical chloride ion concentration of steel bars is not a fixed value under the influence of various factors. In view of this, how to set the critical chloride ion concentration for reinforced concrete structure projects under different service environments to realize timely degradation warning and accurately predict the remaining service life of concrete structures is a problem urgently to be solved in the scientific community and engineering sector at present.

SUMMARY

To overcome the defects of existing warning systems, the invention provides a life-cycle performance intelligent-sensing and degradation warning system and method for concrete structures, which can synchronously monitor, store and transmit the internal micro-environment and steel-bar corrosion condition in reinforced concrete structures in real time and dynamically obtain the critical chloride ion concentration of the structures, thus timely grasping the health status of the structures, giving a degradation warning in time and accurately predicting the remaining service life of the structures to provide scientific references for durability evaluation, protection and rehabilitation of the structures.

The invention is implemented through the following technical solution: a life-cycle performance intelligent-sensing and degradation warning system includes a main control module, a multifunctional sensor module, an anti-theft module and a critical warning module, wherein the multifunctional sensor module, the anti-theft module and the critical warning module are all connected to the main control module, and the main control module analyzes and processes data acquired by the multifunctional sensor module and realizes a timely safety warning through the critical warning module;

The multifunctional sensor module is pre-embedded in a concrete structure and includes a temperature and humidity sensor, a chloride ion-pH gradient sensor, Hall voltage type steel-bar corrosion sensors, a steel-bar stress sensor and a concrete strain sensor; the temperature and humidity sensor, the steel-bar stress sensor and the concrete strain sensor are used for monitoring the temperature, humidity, and steel-bar stress and strain parameters of the concrete structure, the chloride ion-pH gradient sensor is used for detecting the chlorine ion content and pH at different depths in the concrete structure, and the Hall voltage type steel-bar corrosion sensors are used for measuring the corrosion status and corrosion degree of steel bars;

The anti-theft module includes a network video camera and an anti-theft alarm device, wherein the network video camera is used for realizing video surveillance in a monitoring area, and the anti-theft alarm device is used for sensing personnel close to system equipment and giving a voice alarm to prevent the equipment from being stolen or damaged; the critical warning module is used for giving a warning when the concrete structure degrades into a high-risk state, the high-risk state is a result obtained by modeling analysis of the main control module, and a critical chloride ion concentration is dynamically set according to the chlorine ion content in concrete at a corrosion position.

Furthermore, the main control module includes a data pre-processing module, a dynamic threshold setting module and a warning analysis module, wherein the data pre-processing module is used for pre-processing the data acquired by the multifunctional sensor module, the dynamic threshold setting module is used for dynamically modifying the critical chloride ion concentration of the concrete structure in a corresponding service condition based on the chloride ion concentration corrected by the data pre-processing module, and setting critical values of steel-bar stress and concrete strain, and the warning analysis module is used for comparing the pre-processed data with data set by the dynamic threshold setting module to obtain a warning result and transmitting the warning result to the critical warning module to give an alarm.

Furthermore, the chloride ion-pH gradient sensor includes a cylindrical main part, Ag/AgCl electrodes, Ir/IrOx-pH electrodes and a reference electrode corresponding to the Ag/AgCl electrodes and the Ir/IrOx-pH electrodes are arranged on the cylindrical main part, multiple layers of circular grooves are formed in an outer surface of the cylindrical main part in a circumferential direction, wire holes communicated with the cylindrical main part in a thickness direction are reserved in the circular grooves, wire grooves corresponding to the circular grooves are formed inside the cylindrical main part, and the Ag/AgCl electrodes and the Ir/IrOx-pH electrodes are semicircular and are fixed in the circular grooves.

Furthermore, the data pre-processing module further includes a data correction module for correcting data acquired by the chloride ion-pH gradient sensor, and considering the influence of temperature and pH, the data correction module includes a pH influence-based correction module and a temperature influence-based correction module.

Furthermore, the temperature influence-based correction module realizes temperature correction for data measured by Ir/IrOx-pH electrodes and temperature correction for data measured by Ag/AgCl electrodes:

(1) Temperature correction for the data measured by the Ir/IrOx-pH electrodes:

① Measuring potentials of the Ir/IrOx-pH electrodes in concrete under different temperatures by the Ir/IrOx-pH electrodes;

② Linearly fitting the potentials of the Ir/IrOx-pH electrodes measured in Step ① and corresponding measured temperature values to obtain a fitting equation;

③ Obtaining a potential of the Ir/IrOx-pH electrodes under 20° C. according to the fitting equation; and ④ If the potential of the Ir/IrOx-pH electrodes under 20° C. and the pH meet a Nernst equation, determining that the potential y1 of the Ir/IrOx-pH electrodes is linearly correlated with the pH x1, wherein the equation is: $y1=-51.84x1+369.52$;

Obtaining the pH at the position of the Ir/IrOx-pH electrodes in the concrete at this moment according to the potential of the Ir/IrOx-pH electrodes under 20° C. obtained in Step ③ and the equation $y1=-51.84x1+369.52$;

(2) Temperature correction for the data measured by the Ag/AgCl electrodes includes:

① Measuring potentials of the Ag/AgCl electrodes in the concrete under two different temperatures by the Ag/AgCl electrodes;

② Linearly fitting the potentials of the Ag/AgCl electrodes measured in Step ① and corresponding measured temperature values to obtain a fitting equation;

① Obtaining a potential of the Ag/AgCl electrodes under 20° C. according to the fitting equation; and ④ If the potential of the Ag/AgCl electrodes under 20° C. and the chloride ion concentration meet a Nernst equation, determining that the potential y2 of the Ag/AgCl electrodes is linearly correlated with the chloride ion concentration x2, wherein the equation is: $y2=-683.14x2-531.29$;

Obtaining the chloride ion concentration at the position of the Ag/AgCl electrodes in the concrete at this moment according to the potential of the Ag/AgCl electrodes under 20° C. obtained in Step ③ and the equation $y2=-683.14x2-531.29$.

Furthermore, the pH influence-based correction module realizes pH correction for the data measured by the Ag/AgCl electrodes: the pH in the concrete is measured by the Ir/IrOx-pH electrodes; if the pH is greater than 10.5 and smaller than 13, the potential of the Ag/AgCl electrodes at the same depth at this moment does not need to be corrected; or if the pH is greater than 1 and smaller than 10.5, the potential y3 of the Ag/AgCl electrodes at the same depth at this moment needs to be corrected based on the pH x3 according to an equation: $y3=14.26x3+23.58$.

Furthermore, the warning system further includes a cloud server, and the main control module exchanges data with the cloud server to realize systematic management of the concrete structure and correct, store and update data in time.

The invention further provides a life-cycle performance intelligent-sensing and degradation warning method, including:

Step 1: acquiring status data of a concrete structure based on a multifunctional sensor module, wherein the status data include temperature, humidity, chloride ion concentration, pH, steel-bar corrosion parameters, and steel-bar stress and concrete strain data; and pre-processing the acquired status data of the concrete structure;

Step 2: correcting the acquired pH in the concrete structure based on the temperature, and carrying out temperature correction for data measured by Ir/IrOx-pH electrodes to obtain an accurate pH monitoring result in concrete;

Step 3: correcting acquired chloride ion concentration information in the concrete based on the temperature and the pH to obtain an accurate chloride ion concentration monitoring result in the concrete;

Step 4: when Hall voltage type steel-bar corrosion sensors at a depth monitor that steel bars are corroded, automatically taking, by a warning system, a chloride ion concentration measured by a chloride ion-pH gradient sensor at this depth as a critical chloride ion concentration, and inputting the critical chloride ion concentration to a critical warning module; and Step 5: comparing concrete status monitoring results with the critical chloride ion concentration set in Step 4, and the measured steel-bar stress, concrete strain, and temperature and humidity in the concrete to calculate a failure probability of the structure based on a life prediction model, predict the remaining service life of the structure and give a safety warning in time.

Furthermore, in Step 2, when the acquired pH in the concrete structure is corrected based on the temperature, temperature correction for data measured by Ir/IrOx-pH electrodes mainly includes:

① Measuring potentials of the Ir/IrOx-pH electrodes in the concrete under different temperatures by the Ir/IrOx-pH electrodes;

② Linearly fitting the potentials of the Ir/IrOx-pH electrodes measured in Step ① and corresponding measured temperature values to obtain a fitting equation;

③ Obtaining a potential of the Ir/IrOx-pH electrodes under 20° C. according to the fitting equation; and ④ If the potential of the Ir/IrOx-pH electrodes under 20° C. and the pH meet a Nernst equation, determining that the potential $y1$ of the Ir/IrOx-pH electrodes is linearly correlated with the pH $x1$, wherein the equation is: $y1=-51.84x1+369.52$;

obtaining the pH at the position of the Ir/IrOx-pH electrodes in the concrete at this moment according to the potential of the Ir/IrOx-pH electrodes under 20° C. obtained in Step ③ and the equation $y1=-51.84x1+369.52$.

Furthermore, in Step 3, when the acquired chloride ion concentration information in the concrete is corrected based on the temperature and the pH, temperature and pH correction for data measured by the Ag/AgCl electrodes mainly includes:

① Measuring potentials of the Ag/AgCl electrodes in the concrete under two different temperatures by the Ag/AgCl electrodes;

② Linearly fitting the potentials of the Ag/AgCl electrodes measured in Step ① and corresponding measured temperature values to obtain a fitting equation;

③ Obtaining a potential of the Ag/AgCl electrodes under 20° C. according to the fitting equation;

④ If the potential of the Ag/AgCl electrodes under 20° C. and the chloride ion concentration meet a Nernst equation, determining that the potential $y2$ of the Ag/AgCl electrodes is linearly correlated with the chloride ion concentration $x2$, wherein the equation is: $y2=-683.14x2-531.29$;

obtaining the chloride ion concentration at the position of the Ag/AgCl electrodes in the concrete at this moment according to the potential of the Ag/AgCl electrodes under 20° C. obtained in Step ③ and the equation $y2=-683.14x2-531.29$; and ⑤ Measuring the pH in the concrete by the Ir/IrOx-pH electrodes:

If the pH is greater than 10.5 and smaller than 13, a potential of the Ag/AgCl electrodes at a same depth at this moment does not need to be corrected; or if the pH is greater than 1 and smaller than 10.5, the potential $y3$ of the Ag/AgCl electrodes at the same depth at this moment needs to be corrected based on the pH $x3$ according to the equation: $y3=14.26x3+23.58$.

Compared with the prior art, the invention has the following advantages and beneficial effects:

According to the solution of the invention, environmental parameters in concrete are monitored by the multifunctional sensor module, the chlorine ion content and pH at different depths in the concrete are accurately measured by the chlorine iron-pH gradient sensor and the temperature and humidity sensor at this position, and the corrosion status and corrosion degree of steel bars at different depths in a concrete structure can be accurately obtained in situ by the Hall voltage type steel-bar corrosion sensors arranged in a trapezoid;

Moreover, the critical chloride ion concentration of the structure in the corresponding service condition can be obtained according the corrosion condition of steel bars at a certain depth in the concrete structure and the chloride ion concentration and pH at this depth, and thus, an accurate critical value is provided for degradation warning of the structure; the remaining service life of the structure can be accurately predicted through a life prediction model according to the temperature, humidity, chloride ion concentration and pH at different depths, and the critical chloride ion concentration and structure stress condition that are dynamically obtained, and scientific references are provided for durability evaluation, protection and restoration of the structure;

In addition, during warning analysis, a targeted correction method is designed, and temperature and pH correction is carried out for real-time monitoring data of the chloride ion sensor to further guarantee the accuracy of monitoring data; the dynamic critical chloride ion concentration test method provided by the invention overcomes the defects of a preset critical chloride ion concentration and greatly improves the accuracy of degradation warning; and the cloud server is designed, system data can be uploaded to the cloud server in real time to be managed in a unified manner by the cloud server, and an anti-theft effect is realized based on remote monitoring, such that the practical value and economic value are high.

DETAILED DESCRIPTION OF THE EMBODIMENTS

To gain a better understanding of the purposes and advantages of the invention, specific implementations of the invention will be described in detail below in conjunction with the accompanying drawings.

Figure 1:
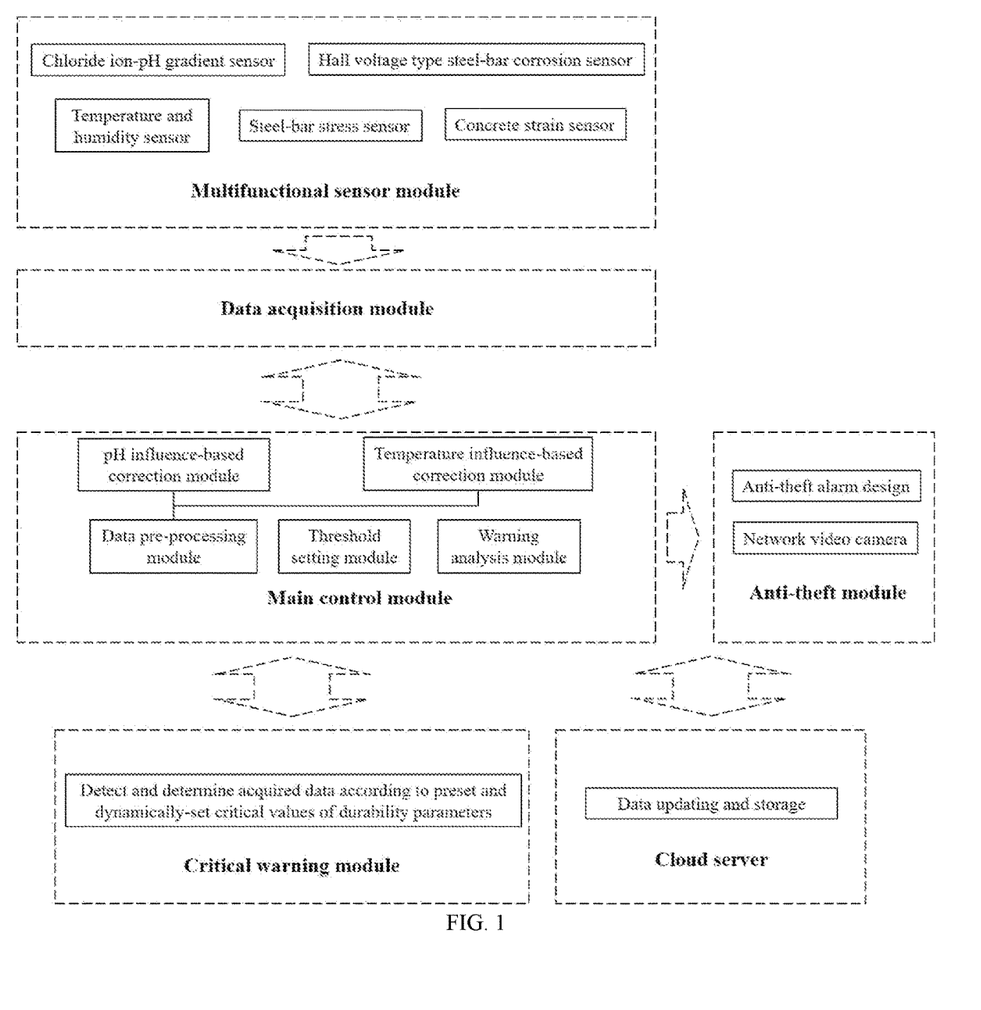
FIG. 1 is a functional block diagram of an intelligent-sensing and degradation warning system in one embodiment of the invention.

Embodiment 1: This embodiment discloses a life-cycle performance intelligent-sensing and degradation warning system for concrete structures. As shown in FIG. 1, the system includes a main control module, a multifunctional sensor module, an anti-theft module and a critical warning module, wherein the multifunctional sensor module, the anti-theft module and the critical warning module are all connected to the main control module; the multifunctional sensor module is pre-embedded in a concrete structure and includes a temperature and humidity sensor, a chloride ion-pH gradient sensor, Hall voltage type steel-bar corrosion sensors, a steel-bar stress sensor and a concrete strain sensor, wherein the temperature and humidity sensor, the steel-bar stress sensor and the concrete strain sensor are used to monitor parameters of concrete such as temperature, humidity, steel-bar stress and concrete strain, the chloride ion-pH gradient sensor is used to detect the chloride ion content and pH at different depths in the concrete, and the Hall voltage type steel-bar corrosion sensors are used to accurately measure the corrosion condition and corrosion degree of steel bars based on the electromagnetic theory and the principle of Shannon entropy.

Figure 2:
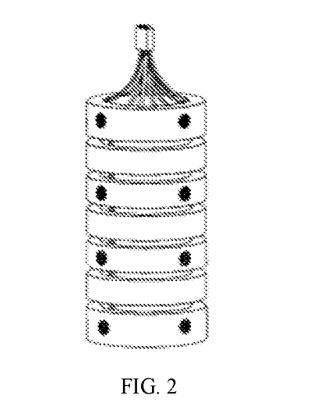
FIG. 2 is a perspective view of a chloride ion-pH gradient sensor in one embodiment of the invention.
Figure 3:
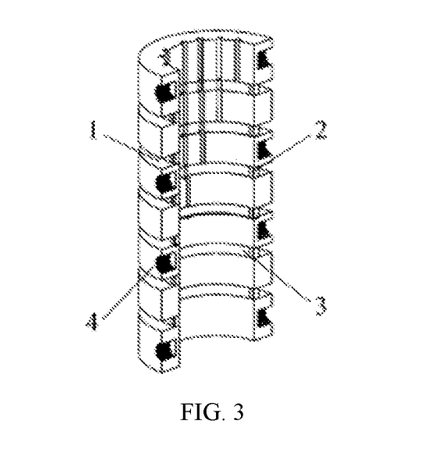
FIG. 3 is a sectional view of the chloride ion-pH gradient sensor.

As shown in FIG. 2 and FIG. 3 which are structural diagrams of the chloride ion-pH gradient sensor, the chloride ion-pH gradient sensor includes a cylindrical main part, wherein Ag/AgCl electrodes, Ir/IrOx-pH electrodes and a reference electrode corresponding to the Ag/AgCl electrodes and the Ir/IrOx-pH electrodes are arranged on the cylindrical main part, multiple layers of circular grooves 1 are formed in the outer surface of the cylindrical main part in a circumferential direction, wire holes 2 communicated with the cylindrical main part in a thickness direction are reserved in the circular grooves 1, wire grooves 3 corresponding to the circular grooves 1 are formed inside the cylindrical main part, and the Ag/AgCl electrodes and the Ir/IrOx-pH electrodes are semicircular and are fixed in the circular grooves 1; one end of each Ag/AgCl electrode and one end of each Ir/IrOx-pH electrode are connected to a wire, which is inserted into one wire hole 2 and is guided out via one wire groove 3 to an aviation plug at the top, the aviation plug is plugged into a corresponding aviation socket on a data acquisition box, data are transmitted to a chloride ion-pH gradient sensor module in the data acquisition box, an acquired signal is converted into the chloride ion concentration and pH by filtering and correction, and the wire grooves 3 are sealed with epoxy resin after the wires are laid therein.

The reference electrode corresponding to the Ag/AgCl electrodes and the Ir/IrOx-pH electrodes is arranged in the middle of the cylindrical main part and is an Mn/MnO$_2$ solid reference electrode with a diameter of 30 mm and a height of 50 mm; and after the Mn/MnO$_2$ solid reference electrode is disposed in the middle of the cylindrical main part, epoxy resin is poured into the cylindrical main part. In this solution, only one reference electrode is adopted, such that errors caused by too many reference electrodes are avoided. In addition, threaded holes 4 are formed in the surface of the cylindrical main part. In actual use, the cylindrical main part can be fixed to steel bars around by means of plastic screws to determine the position of the chloride ion-pH gradient sensor in concrete, such that the chlorine ion content and pH at different depths in the concrete can be accurately measured.

In this solution, Ag/AgCl electrodes are prepared through an anodic polarization method, the current density, as a polarization parameter, is 0.5 mA/cm$^2$, the polarization time is 2.5 hrs, and after being prepared, the electrodes need to be activated in a saturated calcium hydroxide solution for over 30 days before use to ensure the accuracy of test data; and the Ir/IrOx-pH electrodes are prepared through a high-temperature carbonic acid oxidization method by burying Ir filaments into lithium carbonate and then transferring the Ir filaments into a high-temperature furnace to be oxidized under a high temperature of 850° C. for 5 hrs, and after being prepared, the electrodes need to be activated in a saturated calcium hydroxide solution for over 20 days before use to ensure the accuracy of test data.

In this solution, the specific dimensions of the chloride ion-pH gradient sensor are designed as follows: the diameter of the cylindrical main part is 80 mm, seven layers of circular grooves are designed totally, the distance between every two adjacent layers of working electrodes is 10 mm (the distance can be adjusted as actually needed by a project), the depth of the threaded holes is 6 mm, the diameter of the threaded holes is 6 mm, and the diameter of the wire grooves is 5 mm.

Figure 4:
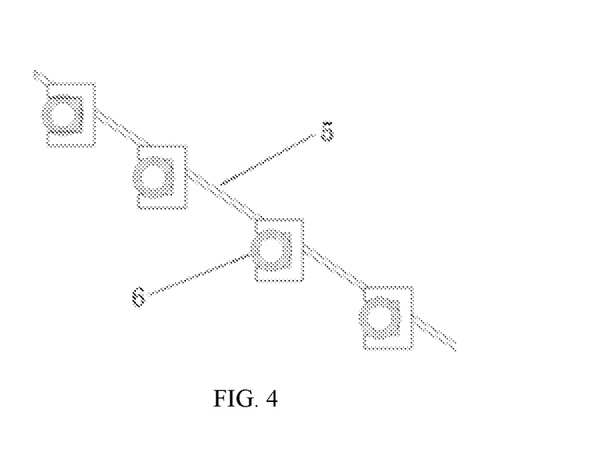
FIG. 4 is Hall voltage type steel-bar corrosion sensors arranged in a trapezoid.

As shown in FIG. 4 which is an installation structural diagram of the Hall voltage type steel-bar corrosion sensors arranged in a trapezoid, a fixing support 6 and the Hall voltage type steel-bar corrosion sensors 6 are configured. The fixing support 5 can adjust the positions of the Hall voltage type steel-bar corrosion sensors 6 freely according to actual test requirements, and the burial depth of the Hall voltage type steel-bar corrosion sensors 6 is the same as that of all layers of sensors in the chloride ion-pH gradient sensor. Each Hall voltage type steel-bar corrosion sensor 6 is internally provided with a pair of Hall sensors and can accurately measure the corrosion degree of a steel bar clamped at the front end thereof. A measured steel bar fixing device is arranged on two sides of each Hall voltage type steel-bar corrosion sensor 6, is composed of two pairs of elastic anti-skid fixing devices and can fix steel bars of any sizes to the Hall sensors at the front end of the Hall voltage type steel-bar corrosion sensor 6.

An actual critical chloride ion concentration in the concrete structure can be dynamically obtained based on measurement results of the chloride ion-pH gradient sensor and the Hall voltage type steel-bar corrosion sensors arranged in a trapezoid. Specifically:

The corrosion status and corrosion degree of steel bars in concrete can be accurately obtained by the Hall voltage type steel-bar corrosion sensors arranged in a trapezoid, and when the Hall voltage type steel-bar corrosion sensors arranged in a trapezoid monitor that the steel bars at a certain depth in the concrete are corroded, the chloride ion concentration measured by the chloride ion-pH gradient sensor at the same time and the same depth is checked and used as the critical chloride ion concentration of the structure in the corresponding service condition.

Referring to FIG. 1 again, the anti-theft module includes a network video camera and an anti-theft alarm device, wherein the network video camera is used for realizing video surveillance in a monitoring area, and the anti-theft alarm device is used for sensing personnel close to system equipment and giving a voice alarm to prevent the equipment from being stolen or damaged; the critical warning module is used for realizing an early warning when the concrete structure degrades to a high risk state. The high risk state is a result obtained based on modeling analysis, the critical chloride ion concentration is dynamically set according to the chloride ion concentration in concrete at a corrosion position, and the main control module is used for analyzing and processing data acquired by the multifunctional sensor module and realizing a timely safety warning through the critical warning module.

Specifically, the main control module includes a data pre-processing module, a dynamic threshold setting module and a warning analysis module. The data pre-processing module is used for pre-processing the data acquired by the multifunctional sensor module as follows: temperature and humidity data acquired by a temperature and humidity probe are directly converted into a digital quantity, and data conversion results are summarized to a main control circuit board through an IIC bus; a temperature sensor acquires data by means of a PT1000 thermal resistor, the resistance of the sensor changes with the variation of temperature, the sensor is connected in series to a main control circuit, a voltage value is obtained by ADC, the current resistance of the sensor is obtained by calculation, the current temperature is obtained by looking up a table, and the temperature is directly acquired by a chip of the main control circuit board; concrete strain and steel-bar stress signals are acquired by a sinusoidal signal acquisition module, and a frequency output by a sensor is acquired and is summarized to the main control circuit board through a 485 bus; signals acquired by chloride ion sensors, pH sensors and the Hall voltage type steel-bar corrosion sensors are subjected to voltage follow-up and amplification by means of an operational amplifier, voltage conversion is carried out directly by an ADC acquisition module of a master micro control unit to obtain a voltage value, and average filtering is carried out on the voltage values obtained by five times of voltage conversion. The master micro control unit of the main control circuit board summarizes all signal acquisition data, and then the data are packed to be transmitted to a GPRS data remote transmission module and are then transmitted to a cloud server by the GPRS module; and after receiving the data, the cloud server carries out protocol analysis on the data and then outputs the analyzed data, and finally, the data are stored in a database.

In addition, in this embodiment, the warning system further includes the cloud server, and the main control module exchanges data with the cloud server to realize systematic management of the reinforced concrete structure and realize data correction, storage and updating. After being uploaded to a platform, acquired data are processed by local PC software according to warning thresholds of the monitored parameters; and if relevant parameters exceed the thresholds, warning information will be automatically pushed to a system administrator, and then the system administrator makes a further judgment and carries out further processing.

After the local PC software acquires data from the cloud server through the network, original data acquired by the sensors are converted into actual physical signals according to a data conversion relation obtained by test, and the data are displayed by software. The dynamic threshold setting module dynamically modifies the critical chloride ion concentration of the structure in the corresponding service condition according to the critical chloride ion concentration determining method described above, and sets critical values of steel-bar stress and concrete strain. The warning analysis module is used for comparing the pre-processed data with data set by the dynamic threshold setting module to obtain a warning result and transmitting the warning result to the critical warning module to give an alarm. Considering the distinctiveness of the chloride ion-pH gradient sensor adopted in this solution, namely the influence of temperature and pH on data measured by the Ag/AgCl electrodes, data acquired by the chloride ion-pH gradient sensor need to be corrected, so the data pre-processing module further includes a data correction module for correcting the data acquired by the chloride ion-pH gradient sensor. Mainly considering the influence of temperature and pH, the data correction module includes a pH influence-based correction module and a temperature influence-based correction module, and the correction principle is as follows:

(1) Temperature correction for data measured by the Ir/IrOx-pH electrodes includes the following steps:

As can be known by experimental modeling, the test potential of the Ir/IrOx-pH electrodes in this solution is linearly correlated with the temperature and the linearly dependent coefficient varies under different pH conditions, so when these electrodes are used for measuring pH in concrete, temperature correction needs to be carried out, specifically:

① Potentials of the Ir/IrOx-pH electrodes in concrete under two different temperatures are measured by the Ir/IrOx-pH electrodes;

② The potentials of the Ir/IrOx-pH electrodes measured in Step ① and corresponding measured temperature values are linearly fitted to obtain a fitting equation;

③ The potential of the Ir/IrOx-pH electrodes under the temperature of 20° C. is obtained according to the fitting equation; and ④ If the potential of the Ir/IrOx-pH electrodes under the temperature of 20° C. and the pH meet the Nernst equation, the potential ($y_1$) of the Ir/IrOx-pH electrodes is linearly correlated with the pH ($x_1$), and the equation is: $y_1=-51.84x_1+369.52$.

The pH at the position of the Ir/IrOx-pH electrodes in the concrete at this moment is obtained by conversion according to the potential of the Ir/IrOx-pH electrodes under the temperature of 20° C. obtained in Step ③ and the equation $y_1=-51.84x_1+369.52$.

(2) Temperature correction for data measured by the Ag/AgCl electrodes includes the following steps:

In addition, the test potential of the Ag/AgCl electrodes in this solution is linearly correlated with the temperature and the linearly dependent coefficient varies under different temperatures, so when these electrodes are used for testing the chloride ion concentration in concrete, temperature correction needs to be carried out, specifically:

① Potentials of the Ag/AgCl electrodes in concrete under two different temperatures are measured by the Ag/AgCl electrodes;

② The potentials of the Ag/AgCl electrodes measured in Step ① and corresponding measured temperature values are linearly fitted to obtain a fitting equation;

③ The potential of the Ag/AgCl electrodes under the temperature of 20° C. is obtained according to the fitting equation; and ④ If the potential of the Ag/AgCl electrodes under the temperature of 20° C. and the chloride ion concentration meet the Nernst equation, the potential ($y_2$) of the Ag/AgCl electrodes is linearly correlated with the chloride ion concentration ($x_2$), and the equation is: $y_2=-683.14x_2-531.29$.

The chloride ion concentration at the position of the Ag/AgCl electrodes in the concrete at this moment is obtained by conversion according to the potential of the Ag/AgCl electrodes under the temperature of 20° C. obtained in Step ③ and the equation $y_2=-683.14x_2-531.29$.

(3) pH correction for data measured by the Ag/AgCl electrodes includes the following steps:

Studies indicate that the test potential of the Ag/AgCl electrodes in this solution is influenced by the pH. When the pH is greater than 1 and smaller than 10.5, the potential of the electrodes increases linearly along with the increase of the pH; and when the pH is greater than 10.5 and smaller than 13, the potential of the electrodes will not be influenced by the pH. So, if these electrodes are used for testing the chloride ion concentration in concrete, pH correction needs to be carried out.

① The pH in concrete is measured by the Ir/IrOx-pH electrodes;

② If the pH is greater than 10.5 and smaller than 13, the potential of the Ag/AgCl electrodes at the same depth at this moment does not need to be corrected; or ③ If the pH is greater than 1 and smaller than 10.5, the potential (y3) of the Ag/AgCl electrodes at the same depth at this moment needs to be corrected based on the pH x3 according to the equation: $y3=14.26x3+23.58$.

By correcting the above data, more accurate monitoring data can be obtained to provide accurate data guarantee for accurate warning.

Embodiment 2: This embodiment discloses a corresponding warning method based on the life-cycle performance intelligent-sensing and degradation warning system for concrete structures in Embodiment 1. The method specifically includes the following steps:

Step 1: concrete status data are acquired based on the multifunctional sensor module, wherein the concrete status data include temperature, humidity, chloride ion concentration, pH, steel-bar corrosion parameters, and steel-bar stress and concrete strain data; the acquired concrete status data are pre-processed;

Step 2: the acquired pH in concrete is corrected based on the temperature to obtain an accurate pH monitoring result in the concrete;

Step 3, acquired chloride ion concentration information in the concrete is corrected based on the temperature and the pH to obtain an accurate chloride ion concentration monitoring result in the concrete;

Step 4: when the Hall voltage type steel-bar corrosion sensors at a certain depth monitor that steel bars are corroded, the system automatically takes the chloride ion concentration measured by the chloride iron-pH gradient sensor at this depth as a critical chloride iron concentration which is input to the critical warning module; and Step 5: concrete status monitoring results are compared with the critical chloride iron concentration dynamically set in Step 4 and the measured parameters such as the steel-bar stress, the concrete strain and the temperature and humidity in the concrete to predict the remaining service life of a concrete structure to give a safety warning in time.

Wherein, in Step 1, the multifunctional sensor module is pre-embedded in the concrete and includes the temperature and humidity sensor, the chloride ion-pH gradient sensor, the Hall voltage type steel-bar corrosion sensors, the steel-bar stress sensor and the concrete strain sensor, wherein the temperature and humidity sensor, the steel-bar stress sensor and the concrete strain sensor are used to monitor status information such as temperature, humidity, steel-bar stress and concrete strain at different depths in the concrete, the Hall voltage type steel-bar corrosion sensors are used to accurately measure the corrosion condition and corrosion degree of steel bars at different depths in the concrete based on the electromagnetic theory and the principle of Shannon entropy, and the chloride ion-pH gradient sensor is used to detect the chloride ion content and pH at different depths in the concrete.

In Step 2, temperature correction for data measured by the Ir/IrOx-pH electrodes mainly includes the following steps:

① Potentials of the Ir/IrOx-pH electrodes in the concrete under two different temperatures are measured by the Ir/IrOx-pH electrodes;

② The potentials of the Ir/IrOx-pH electrodes measured in Step ① and corresponding measured temperature values are linearly fitted to obtain a fitting equation;

③ The potential of the Ir/IrOx-pH electrodes under the temperature of 20° C. is obtained according to the fitting equation; and ④ If the potential of the Ir/IrOx-pH electrodes under the temperature of 20° C. and the pH meet the Nernst equation, the potential (y1) of the Ir/IrOx-pH electrodes is linearly correlated with the pH (x1), and the equation is: $y1=-51.84x1+369.52$; the pH at the position of the Ir/IrOx-pH electrodes in the concrete at this moment is obtained by conversion according to the potential of the Ir/IrOx-pH electrodes under the temperature of 20° C. obtained in Step ③ and the equation $y1=-51.84x1+369.52$.

In Step 3, temperature and pH correction for data measured by the Ag/AgCl electrodes mainly includes the following steps:

① Potentials of the Ag/AgCl electrodes in concrete under two different temperatures are measured by the Ag/AgCl electrodes;

② The potentials of the Ag/AgCl electrodes measured in Step ① and corresponding measured temperature values are linearly fitted to obtain a fitting equation;

③ The potential of the Ag/AgCl electrodes under the temperature of 20° C. is obtained according to the fitting equation;

④ If the potential of the Ag/AgCl electrodes under the temperature of 20° C. and the chloride ion concentration meet the Nernst equation, the potential (y2) of the Ag/AgCl electrodes is linearly correlated with the chloride ion concentration (x2), and the equation is: $y2=-683.14x2-531.29$; the chloride ion concentration at the position of the Ag/AgCl electrodes in the concrete at this moment is obtained by conversion according to the potential of the Ag/AgCl electrodes under the temperature of 20° C. obtained in Step ③ and the equation $y2=-683.14x2-531.29$;

⑤ The pH in the concrete is measured by the Ir/IrOx-pH electrodes;

⑥ If the pH is greater than 10.5 and smaller than 13, the potential of the Ag/AgCl electrodes at the same depth at this moment does not need to be corrected; or ⑦ If the pH is greater than 1 and smaller than 10.5, the potential (y3) of the Ag/AgCl electrodes at the same depth at this moment needs to be corrected based on the pH (x3) according to the equation: $y3=14.26x3+23.58$.

In addition, in Step 4, a critical chloride ion concentration is dynamically set to the critical warning module according to the chloride ion concentration at the steel-bar corrosion position; and then, in Step 5, the concrete status monitoring results are compared with the critical chloride iron concentration dynamically set in Step 4 and the measured parameters such as the steel-bar stress, the concrete strain and the temperature and humidity in the concrete to obtain a failure probability of the concrete structure according to a life prediction model and predict the remaining service life of the concrete structure to give a safety warning in time.

The above embodiments are merely preferred ones of the invention, and are not intended to limit the invention in any form. Any skilled in the art can obtain equivalent embodiments by changing or modifying the technical contents disclosed above and apply these equivalent embodiments to other fields. All simple modifications and equivalent variations and transformations made according to the technical essence of the invention without departing from the contents of the technical solutions of the invention still fall within the protection scope of the technical solutions of the invention.

What is claimed is:

1. A life-cycle performance intelligent-sensing and degradation warning system for a concrete structure, comprising a main control module, a multifunctional sensor module, an anti-theft module and a critical warning module, wherein the multifunctional sensor module, the anti-theft module and the critical warning module are all connected to the main control module, and the main control module analyzes and processes data acquired by the multifunctional sensor module and realizes a timely safety warning through the critical warning module;

the multifunctional sensor module is pre-embedded in a concrete structure and comprises a temperature and humidity sensor, a chloride ion-pH gradient sensor, Hall voltage type steel-bar corrosion sensors, a steel-bar stress sensor and a concrete strain sensor; the temperature and humidity sensor, the steel-bar stress sensor and the concrete strain sensor are used for monitoring a temperature, a humidity, and steel-bar stress and strain parameters of the concrete structure, the chloride ion-pH gradient sensor is used for detecting a chlorine ion content and a pH at different depths in the concrete structure, and the Hall voltage type steel-bar corrosion sensors are used for measuring a corrosion status and a corrosion degree of steel bars;

the anti-theft module comprises a network video camera and an anti-theft alarm device, wherein the network video camera is used for realizing video surveillance in a monitoring area, and the anti-theft alarm device is used for sensing personnel close to system equipment and giving a voice alarm to prevent the equipment from being stolen or damaged; the critical warning module is used for giving a warning when the concrete structure degrades into a high-risk state, the high-risk state is a result obtained by modeling analysis of the main control module, and a critical chloride ion concentration is dynamically set according to the chlorine ion content in concrete at a corrosion position;

the main control module comprises a data pre-processor, a dynamic threshold setter and a warning analyzer, wherein the data pre-processor module is used for pre-processing the data acquired by the multifunctional sensor module, the dynamic threshold setter is used for dynamically modifying the critical chloride ion concentration of the concrete structure in a corresponding service condition based on the chloride ion concentration corrected by the data pre-processor, and setting critical values of steel-bar stress and concrete strain, and the warning analyzer is used for comparing the pre-processed data with data set by the dynamic threshold setter to obtain a warning result and transmitting the warning result to the critical warning module to give an alarm;

the data pre-processor further comprises a data corrector for correcting data acquired by the chloride ion-pH gradient sensor, and considering an influence of the temperature and the pH; the data corrector comprises a pH influence-based correction module and a temperature influence-based correction module;

the temperature influence-based correction module realizes temperature correction for data measured by Ir/IrOx-pH electrodes and temperature correction for data measured by Ag/AgCl electrodes:

(1) temperature correction for the data measured by the Ir/IrOx-pH electrodes:
① measuring potentials of the Ir/IrOx-pH electrodes in the concrete under different temperatures by the Ir/IrOx-pH electrodes;
② linearly fitting the potentials of the Ir/IrOx-pH electrodes measured in step ① and corresponding measured temperature values to obtain a fitting equation;
③ obtaining a potential of the Ir/IrOx-pH electrodes under 20° C. according to the fitting equation; and
④ if the potential of the Ir/IrOx-pH electrodes under 20° C. and the pH meet a Nernst equation, determining that the potential y1 of the Ir/IrOx-pH electrodes is linearly correlated with the pH x1, wherein the equation is: $y1=-51.84x1+369.52$;

obtaining the pH at the position of the Ir/IrOx-pH electrodes in the concrete at this moment according to the potential of the Ir/IrOx-pH electrodes under 20° C. obtained in step ③ and the equation $y1=-51.84x1+369.52$;

(2) temperature correction for the data measured by the Ag/AgCl electrodes comprises:
① measuring potentials of the Ag/AgCl electrodes in the concrete under two different temperatures by the Ag/AgCl electrodes;
② linearly fitting the potentials of the Ag/AgCl electrodes measured in step ① and corresponding measured temperature values to obtain a fitting equation;
③ obtaining a potential of the Ag/AgCl electrodes under 20° C. according to the fitting equation; and
④ if the potential of the Ag/AgCl electrodes under 20° C. and the chloride ion concentration meet the Nernst equation, determining that the potential y2 of the Ag/AgCl electrodes is linearly correlated with the chloride ion concentration x2, wherein the equation is: $y2=-683.14x2-531.29$;

obtaining the chloride ion concentration at the position of the Ag/AgCl electrodes in the concrete at this moment according to the potential of the Ag/AgCl electrodes under 20° C. obtained in step ③ and the equation $y2=-683.14x2-531.29$.

2. The life-cycle performance intelligent-sensing and degradation warning system according to claim 1, wherein the chloride ion-pH gradient sensor comprises a cylindrical main part; the Ag/AgCl electrodes, the Ir/IrOx-pH electrodes, and a reference electrode corresponding to the Ag/AgCl electrodes and the Ir/IrOx-pH electrodes are arranged on the cylindrical main part; multiple layers of circular grooves are formed in an outer surface of the cylindrical main part in a circumferential direction; wire holes communicated with the cylindrical main part in a thickness direction are reserved in the circular grooves; wire grooves corresponding to the circular grooves are formed inside the cylindrical main part; and the Ag/AgCl electrodes and the Ir/IrOx-pH electrodes are semicircular and are fixed in the circular grooves.

3. The life-cycle performance intelligent-sensing and degradation warning system for the concrete structure according to claim 1, wherein the pH influence-based correction module realizes pH correction for the data measured by the Ag/AgCl electrodes: the pH in the concrete is measured by the Ir/IrOx-pH electrodes; if the pH is greater than 10.5 and smaller than 13, a potential of the Ag/AgCl electrodes at a same depth at this moment does not need to be corrected; or if the pH is greater than 1 and smaller than 10.5, the potential y3 of the Ag/AgCl electrodes at the same depth at this moment needs to be corrected based on the pH x3 according to an equation: y3=14.26x3+23.58.

4. The life-cycle performance intelligent-sensing and degradation warning system for the concrete structure according to claim 1, wherein the warning system further comprises a cloud server, and the main control module exchanges data with the cloud server to realize systematic management of the concrete structure and correct, store and update data in time.

5. A warning method based on the life-cycle performance intelligent-sensing and degradation warning system for the concrete structure according to claim 1, comprising:
   step 1: acquiring status data of the concrete structure based on the multifunctional sensor module, wherein the status data comprise temperature, humidity, chloride ion concentration, pH, steel-bar corrosion parameters, and steel-bar stress and concrete strain data; and pre-processing the acquired status data of the concrete structure;
   step 2: correcting the acquired pH in the concrete structure based on the temperature, and carrying out temperature correction for data measured by the Ir/IrOx-pH electrodes to obtain an accurate pH monitoring result in concrete;
   ① measuring potentials of the Ir/IrOx-pH electrodes in the concrete under different temperatures by the Ir/IrOx-pH electrodes;
   ② linearly fitting the potentials of the Ir/IrOx-pH electrodes measured in step ① and corresponding measured temperature values to obtain a fitting equation;
   ③ obtaining a potential of the Ir/IrOx-pH electrodes under 20° C. according to the fitting equation; and
   ④ if the potential of the Ir/IrOx-pH electrodes under 20° C. and the pH meet a Nernst equation, determining that the potential y1 of the Ir/IrOx-pH electrodes is linearly correlated with the pH x1, wherein the equation is: y1=−51.84x1+369.52;
   obtaining the pH at the position of the Ir/IrOx-pH electrodes in the concrete at this moment according to the potential of the Ir/IrOx-pH electrodes under 20° C. obtained in step ③ and the equation y1=−51.84x1+369.52;
   step 3: correcting acquired chloride ion concentration information in the concrete based on the temperature and the pH to obtain an accurate chloride ion concentration monitoring result in the concrete;
   step 4: when the Hall voltage type steel-bar corrosion sensors at a depth monitor that steel bars are corroded, automatically taking, by the warning system, a chloride ion concentration measured by the chloride ion-pH gradient sensor at this depth as the critical chloride ion concentration, and inputting the critical chloride ion concentration to the critical warning module; and
   step 5: comparing concrete status monitoring results with the critical chloride ion concentration set in step 4, and the measured steel-bar stress, concrete strain, and temperature and humidity in the concrete to calculate a failure probability of the structure based on a life prediction model, predict a remaining service life of the structure and give a safety warning in time.

6. The warning method based on the life-cycle performance intelligent-sensing and degradation warning system for the concrete structure according to claim 5, wherein in step 3, when the acquired chloride ion concentration information in the concrete is corrected based on the temperature and the pH, temperature and pH correction for data measured by the Ag/AgCl electrodes mainly comprises:
   ① measuring potentials of the Ag/AgCl electrodes in the concrete under two different temperatures by the Ag/AgCl electrodes;
   ② linearly fitting the potentials of the Ag/AgCl electrodes measured in step ① and corresponding measured temperature values to obtain a fitting equation;
   ③ obtaining a potential of the Ag/AgCl electrodes under 20° C. according to the fitting equation;
   ④ if the potential of the Ag/AgCl electrodes under 20° C. and the chloride ion concentration meet the Nernst equation, determining that the potential y2 of the Ag/AgCl electrodes is linearly correlated with the chloride ion concentration x2, wherein the equation is: y2=−683.14x2−531.29;
   obtaining the chloride ion concentration at the position of the Ag/AgCl electrodes in the concrete at this moment according to the potential of the Ag/AgCl electrodes under 20° C. obtained in step ③ and the equation y2=−683.14x2−531.29; and
   ⑤ measuring the pH in the concrete by the Ir/IrOx-pH electrodes:
   if the pH is greater than 10.5 and smaller than 13, a potential of the Ag/AgCl electrodes at a same depth at this moment does not need to be corrected; or if the pH is greater than 1 and smaller than 10.5, the potential y3 of the Ag/AgCl electrodes at the same depth at this moment needs to be corrected based on the pH x3 according to an equation: y3=14.26x3+23.58.

7. The warning method according to claim 5, wherein the chloride ion-pH gradient sensor comprises a cylindrical main part; the Ag/AgCl electrodes, the Ir/IrOx-pH electrodes, and a reference electrode corresponding to the Ag/AgCl electrodes and the Ir/IrOx-pH electrodes are arranged on the cylindrical main part; multiple layers of circular grooves are formed in an outer surface of the cylindrical main part in a circumferential direction; wire holes communicated with the cylindrical main part in a thickness direction are reserved in the circular grooves; wire grooves corresponding to the circular grooves are formed inside the cylindrical main part; and the Ag/AgCl electrodes and the Ir/IrOx-pH electrodes are semicircular and are fixed in the circular grooves.

8. The warning method according to claim 5, wherein the pH influence-based correction module realizes pH correction for the data measured by the Ag/AgCl electrodes: the pH in the concrete is measured by the Ir/IrOx-pH electrodes; if the pH is greater than 10.5 and smaller than 13, a potential of the Ag/AgCl electrodes at a same depth at this moment does not need to be corrected; or if the pH is greater than 1 and smaller than 10.5, the potential y3 of the Ag/AgCl electrodes at the same depth at this moment needs to be corrected based on the pH x3 according to an equation: y3=14.26x3+23.58.

9. The warning method according to claim 5, wherein the warning system further comprises a cloud server, and the main control module exchanges data with the cloud server to realize systematic management of the concrete structure and correct, store and update data in time.

\* \* \* \* \*